US005840569A

United States Patent [19]

Hillman et al.

[11] Patent Number: 5,840,569

[45] Date of Patent: Nov. 24, 1998

[54] HUMAN GTP-BINDING PROTEINS

[75] Inventors: Jennifer L. Hillman, San Jose; Olga Bandman; Phillip R. Hawkins, both of Mountain View; Surya K. Goli, Sunnyvale, all of Calif.

[73] Assignee: Incyte Pharmaceuticals, Inc., Palo Alto, Calif.

[21] Appl. No.: 766,551

[22] Filed: Dec. 12, 1996

[51] Int. Cl.[6] ....................................................... C12N 1/21

[52] U.S. Cl. .................. 435/252.3; 435/69.1; 435/320.1; 536/23.1; 536/23.5; 536/24.32; 536/24.31

[58] Field of Search ................................. 536/23.1, 23.5, 536/24.32, 24.31; 435/69.1, 252.3, 320.1

[56] References Cited

FOREIGN PATENT DOCUMENTS

WO 93/20439 10/1993 WIPO .

OTHER PUBLICATIONS

Munemitsu, S. et al., "Molecular Cloning and Expression of a G25K cDNA, the Human Homolog of the Yeast Cell Cycle Gene CDC42", *Molecular and Cellular Biology*, 10:5977–5982 (1990).

Database EMBL –EMEST2, Entry AA652260, Accession No. AA652260, (1997).

Kaziro, Y. et al., "Structure and function of signal–transducing GTP–binding proteins", *Annu. Rev. Biochem.*, 60: 349–400 (1991).

Simon, M.I. et al., "Diversity of G proteins in signal transduction", *Science*,252 (5007): 802–808 (1991).

van der Voorn, L. et al., "The WD–40 repeat", *FEBS Lett.*, 307 (2): 131–134 (1992).

Clapham, D.E. et al., "New roles for G–Protein beta gamma–dimers in transmembrane signalling", *Nature*, 365 (6445): 403–406 (1993).

Barbacid, M., "ras genes", *Annu. Rev. Biochem.*, 56: 779–827 (1987).

Treisman, R., "Ternary complex factors: growth factor regulated transcriptional activators" *Curr. Opin. Genet. Dev.*, 4 (1) : 96–101 (1994).

Hall, A., "The cellular functions of small GTP–binding proteins", *Science*, 249 (4969): 635–640 (1990).

Scheffzek K. et al., "Crystal structure of the nuclear Ras–related protein Ran in its GDP–bound form" *Nature*, 374(6520): 378–381 (1995).

Katsuhiro, S. et al., "Molecular cloning of the gene for the human placental GTP–binding protein Gp (G25K): Identification of this GTP–binding protein as the homolog of the yeast cell–division–cycle protein CDC42" *Proc. Natl. Acad. Sci. USA*, 87: 9853–9857 (1990).

Chen, D. et al., "Molecular cloning of two novel rab genes from human melanocytes", *Gene*, 174: 129–134 (1996).

Morimoto, B.H. et al., "Molecular cloning of a member of a new class of low–molecular–weight GTP–binding proteins", *Gene & Development*, 5: 2386–2391 (1991).

Reeck et al. (1987) Cell, vol, 50, p. 667.

Hillier et al. (1995) Accession No. T58540, EST Database.

Hillier et al. (1995) Accession No. T58596, EST Database.

*Primary Examiner*—Robert A. Wax
*Assistant Examiner*—Enrique D. Longton
*Attorney, Agent, or Firm*—Sheela Mohan-Peterson; Lucy J. Billings; Incyte Pharmaceuticals, Inc.

[57] ABSTRACT

The present invention provides three novel GTP-binding proteins (designated individually as BND-1, BND-2, and BND-3, and collectively as BND) and polynucleotides which identify and encode BND. The invention also provides genetically engineered expression vectors and host cells comprising the nucleic acid sequences encoding BND and a method for producing BND. The invention also provides for use of BND and agonists, antibodies, or antagonists specifically binding BND, in the prevention and treatment of diseases associated with expression of BND. Additionally, the invention provides for the use of antisense molecules to polynucleotides encoding BND for the treatment of diseases associated with the expression of BND. The invention also provides diagnostic assays which utilize the polynucleotide, or fragments or the complement thereof, and antibodies specifically binding BND.

7 Claims, 9 Drawing Sheets

```
                9           18          27          36          45          54
5' GGG CGT CAA GTG GGT CCC CGG TCG GAA AAA AGC GCG GTT TGG ATG ACA AAC ATT
                                                           M   T   N   I

                63          72          81          90          99          108
   GGG GTG AGC TAC ACC CCC AAC GGC TAC CCC ACC GAG TAC ATC CCT ACT GCC TTC
   G   V   S   Y   T   P   N   G   Y   P   T   E   Y   I   P   T   A   F

                117         126         135         144         153         162
   GAC AAC TTC TCC GCG GTG GTG TCT GTG GAT GGG CGG CCC GTG AGA CTC CAA CTC
   D   N   F   S   A   V   V   S   V   D   G   R   P   V   R   L   Q   L

                171         180         189         198         207         216
   TGT GAC ACT GCC GGA CAG GAT GAA TTT GAC AAG CTG AGG CCT CTC TGC TAC ACC
   C   D   T   A   G   Q   D   E   F   D   K   L   R   P   L   C   Y   T

                225         234         243         252         261         270
   AAC ACA GAC ATC TTC CTG CTC TGC TTC AGT GTC GTG AGC CCC TCA TCC TTC CAG
   N   T   D   I   F   L   L   C   F   S   V   V   S   P   S   S   F   Q

                279         288         297         306         315         324
   AAC GTC AGT GAG AAA TGG GTG CCG GAG ATT CGA TGC CAC TGT CCC AAA GCC CCC
   N   V   S   E   K   W   V   P   E   I   R   C   H   C   P   K   A   P

                333         342         351         360         369         378
   ATC ATC CTA GTT GGA ACG CAG TCG GAT CTC AGA GAA GAT GTC AAA GTC CTC ATT
   I   I   L   V   G   T   Q   S   D   L   R   E   D   V   K   V   L   I

                387         396         405         414         423         432
   GAG TTG GAC AAA TGC AAA GAA AAG CCA GTG CCT GAA GAG GCG GCT AAG CTG TGC
   E   L   D   K   C   K   E   K   P   V   P   E   E   A   A   K   L   C

                441         450         459         468         477         486
   GCC GAG GAA ATC AAA GCC GCC TCC TAC ATC GAG TGT TCA GCC TTG ACT CAA AAA
   A   E   E   I   K   A   A   S   Y   I   E   C   S   A   L   T   Q   K

                495         504         513         522         531         540
   AAC CTC AAA GAG GTC TTT GAT GCA GCC ATC GTC GCT GGC ATT CAA TAC TCG GAC
   N   L   K   E   V   F   D   A   A   I   V   A   G   I   Q   Y   S   D

                549         558         567         576         585         594
   ACT CAG CAA CAG CCA AAG AAG TCT AAA AGC AGG ACT CCA GAT AAA TGA AAA ACC
   T   Q   Q   Q   P   K   K   S   K   S   R   T   P   D   K

                603         612         621         630         639         648
   TCT CCA AGT CCT GGT GGA AGA AGT ACT GCT GTT TCG TAT GAT GCT GGC AAG ACA
```

FIGURE 1A

```
        657          666          675          684          693          702
CCC AGA AAG GCT ATT TTC AGA TGA ATC GAT ATT AGA GCT TAT TAG TGA AAC AAC

        711
TCT TTT ACT GGT GGA C 3'
```

FIGURE 1B

```
                9           18           27           36           45           54
5' GGA NTC GTC CTT CCT TGA ACC CTC TGG GCC AGC CCA GGG CCC GAA GCC CAC CCA

               63           72           81           90           99          108
   CTC GCN TCT CTA GCA GCC GCT CTT GTC CTC TGG GTA CGG CTC GCG GGA GTT TTG

              117          126          135          144          153          162
   GTT ACC ATG GTG AAG CTG GCA GCC AAA TGC ATC CTG GCA GGA GAC CCA GCA GTG
           M   V   K   L   A   A   K   C   I   L   A   G   D   P   A   V

              171          180          189          198          207          216
   GGC AAG ACC GCC CTN GCA CAG ATC TTC CGC AGT GAT GGA GCC CAT TTC CAG AAA
   G   K   T   A   L   A   Q   I   F   R   S   D   G   A   H   F   Q   K

              225          234          243          252          261          270
   AGC TAC ACC CTG ACA ACA GGA ATG GAT TTG GTG GTG AAG ACA GTG CCA GTT CCT
   S   Y   T   L   T   T   G   M   D   L   V   V   K   T   V   P   V   P

              279          288          297          306          315          324
   GAC ACG GGA GAC AGT GTG GAA CTC TTC ATT TTT GAC TCT GCT GGC AAG GAG CTG
   D   T   G   D   S   V   E   L   F   I   F   D   S   A   G   K   E   L

              333          342          351          360          369          378
   TTT TCG GAA ATG CTG GAT AAA TTG TGG GAG AGT CCC AAT GTC TTA TGT CTC GTC
   F   S   E   M   L   D   K   L   W   E   S   P   N   V   L   C   L   V

              387          396          405          414          423          432
   TAT GAT GTG ACC AAT GAA GAA TCC TTC AAC AAC TGC AGC AAG TGG CTG GAG AAG
   Y   D   V   T   N   E   E   S   F   N   N   C   S   K   W   L   E   K

              441          450          459          468          477          486
   GCT CGG TCA CAG GCT CCA GGC ATC TCT CTC CCA GGT GTT TTA GTT GGG AAC AAG
   A   R   S   Q   A   P   G   I   S   L   P   G   V   L   V   G   N   K

              495          504          513          522          531          540
   ACA GAC CTG GCC GGC AGA CGA GCA GTG GAC TCA GCT GAG GCC CGG GCA TGG GCG
   T   D   L   A   G   R   R   A   V   D   S   A   E   A   R   A   W   A

              549          558          567          576          585          594
   CTG GGC CAG GGC CTG GAA TGT TTT GAA ACA TCC GTG AAA GAG ATG GAA AAC TTC
   L   G   Q   G   L   E   C   F   E   T   S   V   K   E   M   E   N   F

              603          612          621          630          639          648
   GAA GCC CCT TTC CAC TGC CTT GCC AAG CAG TTC CAC CAG CTG TAC CGG GAG AAG
   E   A   P   F   H   C   L   A   K   Q   F   H   Q   L   Y   R   E   K
```

FIGURE 2A

```
        657         666         675         684         693         702
GTG GAG GTT TTC CGG GCC CTG GCA TGA CGA GCT GGA GCA GAT CGT GCT GCA CAA
V   E   V   F   R   A   L   A

        711         720         729         738         747         756
CCG GAG AAG ACA GAA TTA CCT CTG CTC TTT TAA TAT ATA ATG ATG GCT TTA AAT

        765         774
AAA ATT AGG AGA AAA TGT AAA  3'
```

FIGURE 2B

```
             9           18           27           36           45           54
5' CAG CAG TCT NCG ATT CCC CAT NAC CAA TTC GGC TNG GGT CTN CGC GGG CCC GGC

             63          72           81           90           99          108
   CCC CAC CAG ACG GGA CTN CCC GNC CCC AAT TNG CGG CCG AAG AGT CTC CTC GCC

            117         126          135          144          153          162
   CCA GAG TCA TCT TNG GGA CGA CCA GGG CCC GGG TGA TTT TGG GCT CGC CGC GGC

            171         180          189          198          207          216
   CCC KGG TGA TTG TTT CAT CTC CGT GGC CCG CGG TGG TCG TAG CGT CTC CGA GAC

            225         234          243          252          261          270
   CGC GGA CTC CCG TAG GTC CCC GTG GCC CCG AGT TGT AGT CGG GAC ACC CCG GCC

            279         288          297          306          315          324
   GCG GGT GAT CGT CGG GTC TCC AAG CGC CCG TCG CTG ACG CGG ATC CGG CCT YGG

            333         342          351          360          369          378
   CGC CTT CTC AGG GGC GCC CTG CAA GGC CGC AGG CAG GAT GAA CAT TCT GGC ACC

            387         396          405          414          423          432
   CGT GCG GAG GGA TCG CGT CCT GGC GGA CTG CCC CAG TGC CTG AGG AAG GAG GCC

            441         450          459          468          477          486
   GCT TTG CAC GGG CAC AAA GAC TTC CAC CCC CGC GTC ACC TGC GCC TGC CAG GAG

            495         504          513          522          531          540
   CAC CGG ACA GGC ACC GTG GGA TTT AAG ATC TCC AAG GTC ATT GTG GTG GGG GAC

            549         558          567          576          585          594
   CTG TCG GTG GGG AAG ACT TGC CTC ATT AAT AGG TTC TGC AAA GAC ACC TTT GAT

         603         612          621          630          639          648
   AAG AAT TAC AAG GCC ACC ATT GGA GTG GAC TTC GAG ATG GAA CGA TTT GAG GTG
                                                    M   E   R   F   E   V
```

FIGURE 3A

```
        657         666         675         684         693         702
CTG GGC ATT CCC TTC AGT TTG CAG CTT TGG GAT ACC GCT GGG CAG GAG AGG TTC
L   G   I   P   F   S   L   Q   L   W   D   T   A   G   Q   E   R   F

        711         720         729         738         747         756
AAA TGC ATT GCA TCA ACC TAC TAT AGA GGA GCT CAA GCC ATC ATC ATT GTC TTC
K   C   I   A   S   T   Y   Y   R   G   A   Q   A   I   I   I   V   F

        765         774         783         792         801         810
AAC CTG AAT GAT GTG GCA TCT CTG GAA CAT ACC AAG CAG TGG CTG GCC GAT GCC
N   L   N   D   V   A   S   L   E   H   T   K   Q   W   L   A   D   A

        819         828         837         846         855         864
CTG AAG GAG AAT GAC CCT TCC AGT GTG CTT CTC TTC CTT GTA GGT TCC AAG AAG
L   K   E   N   D   P   S   S   V   L   L   F   L   V   G   S   K   K

        873         882         891         900         909         918
GAT CTG AGT ACC CCT GCT CAG TAT GCG CTG ATG GAG AAA GAM GCC CTC CAG GTG
D   L   S   T   P   A   Q   Y   A   L   M   E   K   X   A   L   Q   V

        927         936         945         954         963         972
GCC CAG GGG ATG AAG GCT GAG TAC TGG GCA GTC TCA TCT CTC ACT GGT GAG AAT
A   Q   G   M   K   A   E   Y   W   A   V   S   S   L   T   G   E   N

        981         990         999        1008        1017        1026
GTC CGA GAA TTC TTC TTC CGT GTG GCA GCA CTG ACC TTT GAG GCC AAT GTG CTG
V   R   E   F   F   F   R   V   A   A   L   T   F   E   A   N   V   L

       1035        1044        1053        1062        1071        1080
GCT GAG CTG GAG AAA TCG GGG GCT CGA CGC ATT GGG GAT GTT GTC CGC ATC AAC
A   E   L   E   K   S   G   A   R   R   I   G   D   V   V   R   I   N

       1089        1098        1107        1116        1125        1134
AGT GAT GAC AGC AAC CTS TAC CTA ACT GCC AGC AAG AAG AAG CCC ACA TGT TGC
S   D   D   S   N   L   Y   L   T   A   S   K   K   K   P   T   C   C

       1143        1152        1161        1170        1179        1188
CCA TGA GGG CTG AGG AGA CTG TTC AGA GAC TGC CCA GCC CTA GGG CAC TGT GCC
P

       1197        1206        1215        1224        1233        1242
ACC CTC ATT YCT TCA GAG NTT GAC CCC TGG GNG ANT TGC ANT GAC TTT ATT CAG

       1251
ACC AAA GAG GT 3'
```

FIGURE 3B

```
1    M T N I G - - - - - - - - - - - - - - - V S Y T P N G Y P T E Y I P T A F D N F   SEQ ID NO:1
1    M Q T I K C V V V G D G A V G K T C L L I S Y T T N K F P S E Y V P T V F D N Y   GI 183490

26   S A V V S V D G R P V R L Q L C D T A G Q D E F D K L R P L C Y T N T D I F L L   SEQ ID NO:1
41   A V T V M I G G E P Y T L G L F D T A G Q E D Y D R L R P L S Y P Q T D V F L V   GI 183490

66   C F S V V S P S S F Q N V S E K W V P E I R C H C P K A P I I L V G T Q S D L R   SEQ ID NO:1
81   C F S V V S P S S F E N V K E K W V P E I T H H C P K T P F L L V G T Q I D L R   GI 183490

106  E D V K V L I E L D K C K E K P V - P E E A A K L C A E E I K A A S Y I E C S A   SEQ ID NO:1
121  D D P S T I E K L A K N K Q K P I T P E T A E K L - A R D L K A V K Y V E C S A   GI 183490

145  L T Q K N L K E V F D A A I V A G I Q Y S D T Q Q Q P K K S K S R T P D K         SEQ ID NO:1
160  L T Q K G L K N V F D E A I L A A L E - - - - P P E P K K S R - R C V L L         GI 183490
```

FIGURE 4

```
1    M V K - - - - L A A K C I L A G D P A V G K T A L A Q I F R S D G A H F Q K S Y   SEQ ID NO:3
1    M S M E D Y D F L F K I V L I G N A G V G K T C L V R R F - - T Q G L F P P G Q   GI 1457955

37   T L T T G M D L V V K T V P V P D T G D S V E L F I F D S A G K E L F S E M L D   SEQ ID NO:3
39   G A T I G V G F M I K T V E I - - N G E K V K L Q I W D T A G Q E R F R S I T Q   GI 1457955

77   K L W E S P N V L C L V Y D V T N E E S F N N C S K W L E K A R S Q A P G I S L   SEQ ID NO:3
77   S Y Y R S A N A L I L T Y D I T C E E S F R C L P E W L - R E I E Q Y A S N K V   GI 1457955

117  P G V L V G N K T D L A G R R A V D S A E A R A W A L G Q G L E C F E T S V K E   SEQ ID NO:3
116  I T V L V G N K I D L A E R R E V S Q Q R A E E F S E A Q D M Y Y L E T S A K E   GI 1457955

157  M E N F E A P F H C L A K Q F H Q L Y R E K V - - - E V F R A L A               SEQ ID NO:3
156  S D N V E K L F L D L A C R L I S E A R Q N T L V N N V S S P L P G E G K S I S   GI 1457955

186                                                                                  SEQ ID NO:3
196  Y L T C C N F N                                                                 GI 1457955
```

FIGURE 5

```
1   - - - - - - - - - - - - - - - - - - - - - - - - - - - - - - - - - - - - - - - M   SEQ ID NO:5
1   N S K V I V V G D L S V G K T C L I N R F C K D T F D K N Y K A T I G V D F E M   GI 240986

2   E R F E V L G I P F S L Q L W D T A G Q E R F K C I A S T Y Y R G A Q A I I I V   SEQ ID NO:5
41  E R F E V L G V P F S L Q L W D T A G Q E R F K C I A S T Y Y R G A Q A I I I V   GI 240986

42  F N L N D V A S L E H T K Q W L A D A L K E N D P S S V L L F L V G S K K D L S   SEQ ID NO:5
81  F N L N D V A S L E H T K Q W L T D A L K E N D P S N V L L F L V G S K K D L S   GI 240986

82  T P A Q Y A L M E K X A L Q V A Q G M K A E Y W A V S S L T G E N V R E F F F R   SEQ ID NO:5
121 T P A Q Y S L M E K D A L K V A Q E I K A E Y W A V S S L T G E N V R E F F F R   GI 240986

122 V A A L T F E A N V L A E L E K S G A R R I G D V V R I N S D D S N L Y L T A S   SEQ ID NO:5
161 V A A L T F E A N V L A D V E K S G A R H I A D V V R I N S D D K N L Y L T A S   GI 240986

162 K K K P T C C P                                                                   SEQ ID NO:5
201 K K K A T C C P                                                                   GI 240986
```

FIGURE 6

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 181 amino acids
( B ) TYPE: amino acid
( C ) STRANDEDNESS: single
( D ) TOPOLOGY: linear ( v i i ) IMMEDIATE SOURCE:
( A ) LIBRARY: SEQ ID NO:1
( B ) CLONE: 113700

( x i ) SEQUENCE DESCRIPTION: SEQ ID NO:1:

Met Thr Asn Ile Gly Val Ser Tyr Thr Pro Asn Gly Tyr Pro Thr Glu
1 5 10 15

Tyr Ile Pro Thr Ala Phe Asp Asn Phe Ser Ala Val Val Ser Val Asp
20 25 30

Gly Arg Pro Val Arg Leu Gln Leu Cys Asp Thr Ala Gly Gln Asp Glu
35 40 45

Phe Asp Lys Leu Arg Pro Leu Cys Tyr Thr Asn Thr Asp Ile Phe Leu
50 55 60

Leu Cys Phe Ser Val Val Ser Pro Ser Ser Phe Gln Asn Val Ser Glu
65 70 75 80

Lys Trp Val Pro Glu Ile Arg Cys His Cys Pro Lys Ala Pro Ile Ile
85 90 95

Leu Val Gly Thr Gln Ser Asp Leu Arg Glu Asp Val Lys Val Leu Ile
100 105 110

Glu Leu Asp Lys Cys Lys Glu Lys Pro Val Pro Glu Glu Ala Ala Lys
115 120 125

Leu Cys Ala Glu Glu Ile Lys Ala Ala Ser Tyr Ile Glu Cys Ser Ala
130 135 140

Leu Thr Gln Lys Asn Leu Lys Glu Val Phe Asp Ala Ala Ile Val Ala
145 150 155 160

Gly Ile Gln Tyr Ser Asp Thr Gln Gln Gln Pro Lys Lys Ser Lys Ser
165 170 175

Arg Thr Pro Asp Lys
180

( 2 ) INFORMATION FOR SEQ ID NO:2:

( i ) SEQUENCE CHARACTERISTICS:
( A ) LENGTH: 719 base pairs
( B ) TYPE: nucleic acid
( C ) STRANDEDNESS: single
( D ) TOPOLOGY: linear ( v i i ) IMMEDIATE SOURCE:
( A ) LIBRARY: SEQ ID NO:2
( B ) CLONE: 113700

( x i ) SEQUENCE DESCRIPTION: SEQ ID NO:2:

CGGGCGTCAA GTGGGTCCCC GGTCGGAAAA AAGCGCGGTT TGGATGACAA ACATTGGGGT 60

GAGCTACACC CCCAACGGCT ACCCCACCGA GTACATCCCT ACTGCCTTCG ACAACTTCTC 120

CGCGGTGGTG TCTGTGGATG GGCGGCCCGT GAGACTCCAA CTCTGTGACA CTGCCGGACA 180

GGATGAATTT GACAAGCTGA GGCCTCTCTG CTACACCAAC ACAGACATCT TCCTGCTCTG 240

-continued

```
CTTCAGTGTC GTGAGCCCCT CATCCTTCCA GAACGTCAGT GAGAAATGGG TGCCGGAGAT    300
TCGATGCCAC TGTCCCAAAG CCCCCATCAT CCTAGTTGGA ACGCAGTCGG ATCTCAGAGA    360
AGATGTCAAA GTCCTCATTG AGTTGGACAA ATGCAAAGAA AAGCCAGTGC CTGAAGAGGC    420
GGCTAAGCTG TGCGCCGAGG AAATCAAAGC CGCCTCCTAC ATCGAGTGTT CAGCCTTGAC    480
TCAAAAAAAC CTCAAAGAGG TCTTTGATGC AGCCATCGTC GCTGGCATTC AATACTCGGA    540
CACTCAGCAA CAGCCAAAGA AGTCTAAAAG CAGGACTCCA GATAAATGAA AAACCTCTCC    600
AAGTCCTGGT GGAAGAAGTA CTGCTGTTTC GTATGATGCT GGCAAGACAC CCAGAAAGGC    660
TATTTTCAGA TGAATCGATA TTAGAGCTTA TTAGTGAAAC AACTCTTTTA CTGGTGGAC     719
```

( 2 ) INFORMATION FOR SEQ ID NO:3:

( i ) SEQUENCE CHARACTERISTICS:
( A ) LENGTH: 186 amino acids
( B ) TYPE: amino acid
( C ) STRANDEDNESS: single
( D ) TOPOLOGY: linear ( v i i ) IMMEDIATE SOURCE:
( A ) LIBRARY: SEQ ID NO: 3
( B ) CLONE: 538177

( x i ) SEQUENCE DESCRIPTION: SEQ ID NO:3:

```
Met Val Lys Leu Ala Ala Lys Cys Ile Leu Ala Gly Asp Pro Ala Val
 1               5                  10                  15

Gly Lys Thr Ala Leu Ala Gln Ile Phe Arg Ser Asp Gly Ala His Phe
            20                  25                  30

Gln Lys Ser Tyr Thr Leu Thr Thr Gly Met Asp Leu Val Val Lys Thr
        35                  40                  45

Val Pro Val Pro Asp Thr Gly Asp Ser Val Glu Leu Phe Ile Phe Asp
    50                  55                  60

Ser Ala Gly Lys Glu Leu Phe Ser Glu Met Leu Asp Lys Leu Trp Glu
65                  70                  75                  80

Ser Pro Asn Val Leu Cys Leu Val Tyr Asp Val Thr Asn Glu Glu Ser
                85                  90                  95

Phe Asn Asn Cys Ser Lys Trp Leu Glu Lys Ala Arg Ser Gln Ala Pro
            100                 105                 110

Gly Ile Ser Leu Pro Gly Val Leu Val Gly Asn Lys Thr Asp Leu Ala
        115                 120                 125

Gly Arg Arg Ala Val Asp Ser Ala Glu Ala Arg Ala Trp Ala Leu Gly
    130                 135                 140

Gln Gly Leu Glu Cys Phe Glu Thr Ser Val Lys Glu Met Glu Asn Phe
145                 150                 155                 160

Glu Ala Pro Phe His Cys Leu Ala Lys Gln Phe His Gln Leu Tyr Arg
                165                 170                 175

Glu Lys Val Glu Val Phe Arg Ala Leu Ala
            180                 185
```

( 2 ) INFORMATION FOR SEQ ID NO:4:

( i ) SEQUENCE CHARACTERISTICS:
( A ) LENGTH: 779 base pairs
( B ) TYPE: nucleic acid
( C ) STRANDEDNESS: single
( D ) TOPOLOGY: linear ( v i i ) IMMEDIATE SOURCE:
( A ) LIBRARY: SEQ ID NO:4
( B ) CLONE: 538177

( x i ) SEQUENCE DESCRIPTION: SEQ ID NO:4:

```
CCGGANTCGT CCTTCCTTGA ACCCTCTGGG CCAGCCCAGG GCCCGAAGCC CACCCACTCG    60
CNTCTCTAGC AGCCGCTCTT GTCCTCTGGG TACGGCTCGC GGGAGTTTTG GTTACCATGG   120
TGAAGCTGGC AGCCAAATGC ATCCTGGCAG GAGACCCAGC AGTGGGCAAG ACCGCCCTNG   180
CACAGATCTT CCGCAGTGAT GGAGCCCATT TCCAGAAAAG CTACACCCTG ACAACAGGAA   240
TGGATTTGGT GGTGAAGACA GTGCCAGTTC CTGACACGGG AGACAGTGTG GAACTCTTCA   300
TTTTTGACTC TGCTGGCAAG GAGCTGTTTT CGGAAATGCT GGATAAATTG TGGGAGAGTC   360
CCAATGTCTT ATGTCTCGTC TATGATGTGA CCAATGAAGA ATCCTTCAAC AACTGCAGCA   420
AGTGGCTGGA GAAGGCTCGG TCACAGGCTC CAGGCATCTC TCTCCCAGGT GTTTTAGTTG   480
GGAACAAGAC AGACCTGGCC GGCAGACGAG CAGTGGACTC AGCTGAGGCC CGGGCATGGG   540
CGCTGGGCCA GGGCCTGGAA TGTTTTGAAA CATCCGTGAA AGAGATGGAA AACTTCGAAG   600
CCCCTTTCCA CTGCCTTGCC AAGCAGTTCC ACCAGCTGTA CCGGGAGAAG GTGGAGGTTT   660
TCCGGGCCCT GGCATGACGA GCTGGAGCAG ATCGTGCTGC ACAACCGGAG AAGACAGAAT   720
TACCTCTGCT CTTTTAATAT ATAATGATGG CTTTAAATAA AATTAGGAGA AAATGTAAA    779
```

( 2 ) INFORMATION FOR SEQ ID NO:5:

( i ) SEQUENCE CHARACTERISTICS:
( A ) LENGTH: 169 amino acids
( B ) TYPE: amino acid
( C ) STRANDEDNESS: single
( D ) TOPOLOGY: linear ( v i i ) IMMEDIATE SOURCE:
( A ) LIBRARY: SEQ ID NO:5
( B ) CLONE: 627051

( x i ) SEQUENCE DESCRIPTION: SEQ ID NO:5:

```
Met Glu Arg Phe Glu Val Leu Gly Ile Pro Phe Ser Leu Gln Leu Trp
 1               5                  10                  15

Asp Thr Ala Gly Gln Glu Arg Phe Lys Cys Ile Ala Ser Thr Tyr Tyr
            20                  25                  30

Arg Gly Ala Gln Ala Ile Ile Ile Val Phe Asn Leu Asn Asp Val Ala
        35                  40                  45

Ser Leu Glu His Thr Lys Gln Trp Leu Ala Asp Ala Leu Lys Glu Asn
    50                  55                  60

Asp Pro Ser Ser Val Leu Leu Phe Leu Val Gly Ser Lys Lys Asp Leu
65                  70                  75                  80

Ser Thr Pro Ala Gln Tyr Ala Leu Met Glu Lys Xaa Ala Leu Gln Val
                85                  90                  95

Ala Gln Gly Met Lys Ala Glu Tyr Trp Ala Val Ser Ser Leu Thr Gly
            100                 105                 110

Glu Asn Val Arg Glu Phe Phe Phe Arg Val Ala Ala Leu Thr Phe Glu
        115                 120                 125

Ala Asn Val Leu Ala Glu Leu Glu Lys Ser Gly Ala Arg Arg Ile Gly
    130                 135                 140

Asp Val Val Arg Ile Asn Ser Asp Asp Ser Asn Leu Tyr Leu Thr Ala
145                 150                 155                 160

Ser Lys Lys Lys Pro Thr Cys Cys Pro
                165
```

( 2 ) INFORMATION FOR SEQ ID NO:6:

( i ) SEQUENCE CHARACTERISTICS:
( A ) LENGTH: 1255 base pairs
( B ) TYPE: nucleic acid
( C ) STRANDEDNESS: single
( D ) TOPOLOGY: linear ( v i i ) IMMEDIATE SOURCE:
( A ) LIBRARY: SEQ ID NO:6
( B ) CLONE: 627051

( x i ) SEQUENCE DESCRIPTION: SEQ ID NO:6:

```
CAGCAGTCTN CGATTCCCCA TNACCAATTC GGCTNGGGTC TNCGCGGGCC CGGCCCCCAC     60
CAGACGGGAC TNCCCGNCCC CAATTNGCGG CCGAAGAGTC TCCTCGCCCC AGAGTCATCT    120
TNGGGACGAC CAGGGCCCGG GTGATTTTGG GCTCGCCGCG GCCCCKGGTG ATTGTTTCAT    180
CTCCGTGGCC CGCGGTGGTC GTAGCGTCTC CGAGACCGCG GACTCCCGTA GGTCCCCGTG    240
GCCCCGAGTT GTAGTCGGGA CACCCCGGCC GCGGGTGATC GTCGGGTCTC CAAGCGCCCG    300
GGTCGCTGAC GCGGATCCGG CCTYGGCGCC TTCTCAGGGG CGCCCTGCAA GGCCGCAGGC    360
AGGATGAACA TTCTGGCACC CGTGCGGAGG GATCGCGTCC TGGCGGACTG CCCCAGTGCC    420
TGAGGAAGGA GGCCGCTTTG CACGGGCACA AAGACTTCCA CCCCCGCGTC ACCTGCGCCT    480
GCCAGGAGCA CCGGACAGGC ACCGTGGGAT TTAAGATCTC CAAGGTCATT GTGGTGGGGG    540
ACCTGTCGGT GGGGAAGACT TGCCTCATTA ATAGGTTCTG CAAAGACACC TTTGATAAGA    600
ATTACAAGGC CACCATTGGA GTGGACTTCG AGATGGAACG ATTTGAGGTG CTGGGCATTC    660
CCTTCAGTTT GCAGCTTTGG GATACCGCTG GGCAGGAGAG GTTCAAATGC ATTGCATCAA    720
CCTACTATAG AGGAGCTCAA GCCATCATCA TTGTCTTCAA CCTGAATGAT GTGGCATCTC    780
TGGAACATAC CAAGCAGTGG CTGGCCGATG CCCTGAAGGA GAATGACCCT TCCAGTGTGC    840
TTCTCTTCCT TGTAGGTTCC AAGAAGGATC TGAGTACCCC TGCTCAGTAT GCGCTGATGG    900
AGAAAGAMGC CCTCCAGGTG GCCCAGGGGA TGAAGGCTGA GTACTGGGCA GTCTCATCTC    960
TCACTGGTGA GAATGTCCGA GAATTCTTCT TCCGTGTGGC AGCACTGACC TTTGAGGCCA   1020
ATGTGCTGGC TGAGCTGGAG AAATCGGGGG CTCGACGCAT TGGGGATGTT GTCCGCATCA   1080
ACAGTGATGA CAGCAACCTS TACCTAACTG CCAGCAAGAA GAAGCCCACA TGTTGCCCAT   1140
GAGGGCTGAG GAGACTGTTC AGAGACTGCC CAGCCCTAGG GCACTGTGCC ACCCTCATTY   1200
CTTCAGAGNT TGACCCCTGG GNGANTTGCA NTGACTTTAT TCAGACCAAA GAGGT        1255
```

( 2 ) INFORMATION FOR SEQ ID NO:7:

( i ) SEQUENCE CHARACTERISTICS:
( A ) LENGTH: 191 amino acids
( B ) TYPE: amino acid
( C ) STRANDEDNESS: single
( D ) TOPOLOGY: linear ( v i i ) IMMEDIATE SOURCE:
( A ) LIBRARY: GenBank
( B ) CLONE: 183490

( x i ) SEQUENCE DESCRIPTION: SEQ ID NO:7:

```
Met Gln Thr Ile Lys Cys Val Val Val Gly Asp Gly Ala Val Gly Lys
1               5                   10                  15

Thr Cys Leu Leu Ile Ser Tyr Thr Thr Asn Lys Phe Pro Ser Glu Tyr
            20                  25                  30

Val Pro Thr Val Phe Asp Asn Tyr Ala Val Thr Val Met Ile Gly Gly
        35                  40                  45

Glu Pro Tyr Thr Leu Gly Leu Phe Asp Thr Ala Gly Gln Glu Asp Tyr
    50                  55                  60
```

-continued

Asp Arg Leu Arg Pro Leu Ser Tyr Pro Gln Thr Asp Val Phe Leu Val
65 70 75 80

Cys Phe Ser Val Val Ser Pro Ser Ser Phe Glu Asn Val Lys Glu Lys
85 90 95

Trp Val Pro Glu Ile Thr His His Cys Pro Lys Thr Pro Phe Leu Leu
100 105 110

Val Gly Thr Gln Ile Asp Leu Arg Asp Asp Pro Ser Thr Ile Glu Lys
115 120 125

Leu Ala Lys Asn Lys Gln Lys Pro Ile Thr Pro Glu Thr Ala Glu Lys
130 135 140

Leu Ala Arg Asp Leu Lys Ala Val Lys Tyr Val Glu Cys Ser Ala Leu
145 150 155 160

Thr Gln Lys Gly Leu Lys Asn Val Phe Asp Glu Ala Ile Leu Ala Ala
165 170 175

Leu Glu Pro Pro Glu Pro Lys Lys Ser Arg Arg Cys Val Leu Leu
180 185 190

( 2 ) INFORMATION FOR SEQ ID NO:8:

( i ) SEQUENCE CHARACTERISTICS:
( A ) LENGTH: 203 amino acids
( B ) TYPE: amino acid
( C ) STRANDEDNESS: single
( D ) TOPOLOGY: linear ( v i i ) IMMEDIATE SOURCE:
( A ) LIBRARY: GenBank
( B ) CLONE: 1457955

( x i ) SEQUENCE DESCRIPTION: SEQ ID NO:8:

Met Ser Met Glu Asp Tyr Asp Phe Leu Phe Lys Ile Val Leu Ile Gly
1 5 10 15

Asn Ala Gly Val Gly Lys Thr Cys Leu Val Arg Arg Phe Thr Gln Gly
20 25 30

Leu Phe Pro Pro Gly Gln Gly Ala Thr Ile Gly Val Gly Phe Met Ile
35 40 45

Lys Thr Val Glu Ile Asn Gly Glu Lys Val Lys Leu Gln Ile Trp Asp
50 55 60

Thr Ala Gly Gln Glu Arg Phe Arg Ser Ile Thr Gln Ser Tyr Tyr Arg
65 70 75 80

Ser Ala Asn Ala Leu Ile Leu Thr Tyr Asp Ile Thr Cys Glu Glu Ser
85 90 95

Phe Arg Cys Leu Pro Glu Trp Leu Arg Glu Ile Glu Gln Tyr Ala Ser
100 105 110

Asn Lys Val Ile Thr Val Leu Val Gly Asn Lys Ile Asp Leu Ala Glu
115 120 125

Arg Arg Glu Val Ser Gln Gln Arg Ala Glu Glu Phe Ser Glu Ala Gln
130 135 140

Asp Met Tyr Tyr Leu Glu Thr Ser Ala Lys Glu Ser Asp Asn Val Glu
145 150 155 160

Lys Leu Phe Leu Asp Leu Ala Cys Arg Leu Ile Ser Glu Ala Arg Gln
165 170 175

Asn Thr Leu Val Asn Asn Val Ser Ser Pro Leu Pro Gly Glu Gly Lys
180 185 190

Ser Ile Ser Tyr Leu Thr Cys Cys Asn Phe Asn
195 200

-continued ( 2 ) INFORMATION FOR SEQ ID NO:9:

( i ) SEQUENCE CHARACTERISTICS:
( A ) LENGTH: 208 amino acids
( B ) TYPE: amino acid
( C ) STRANDEDNESS: single
( D ) TOPOLOGY: linear ( v i i ) IMMEDIATE SOURCE:
( A ) LIBRARY: GenBank
( B ) CLONE: 240986

( x i ) SEQUENCE DESCRIPTION: SEQ ID NO:9:

Asn Ser Lys Val Ile Val Val Gly Asp Leu Ser Val Gly Lys Thr Cys
1 5 10 15

Leu Ile Asn Arg Phe Cys Lys Asp Thr Phe Asp Lys Asn Tyr Lys Ala
20 25 30

Thr Ile Gly Val Asp Phe Glu Met Glu Arg Phe Glu Val Leu Gly Val
35 40 45

Pro Phe Ser Leu Gln Leu Trp Asp Thr Ala Gly Gln Glu Arg Phe Lys
50 55 60

Cys Ile Ala Ser Thr Tyr Tyr Arg Gly Ala Gln Ala Ile Ile Ile Val
65 70 75 80

Phe Asn Leu Asn Asp Val Ala Ser Leu Glu His Thr Lys Gln Trp Leu
85 90 95

Thr Asp Ala Leu Lys Glu Asn Asp Pro Ser Asn Val Leu Leu Phe Leu
100 105 110

Val Gly Ser Lys Lys Asp Leu Ser Thr Pro Ala Gln Tyr Ser Leu Met
115 120 125

Glu Lys Asp Ala Leu Lys Val Ala Gln Glu Ile Lys Ala Glu Tyr Trp
130 135 140

Ala Val Ser Ser Leu Thr Gly Glu Asn Val Arg Glu Phe Phe Phe Arg
145 150 155 160

Val Ala Ala Leu Thr Phe Glu Ala Asn Val Leu Ala Asp Val Glu Lys
165 170 175

Ser Gly Ala Arg His Ile Ala Asp Val Val Arg Ile Asn Ser Asp Asp
180 185 190

Lys Asn Leu Tyr Leu Thr Ala Ser Lys Lys Lys Ala Thr Cys Cys Pro
195 200 205

HUMAN GTP-BINDING PROTEINS

FIELD OF THE INVENTION

This invention relates to nucleic acid and amino acid sequences of three novel GTP-binding proteins and to the use of these sequences in the diagnosis, prevention, and treatment of disorders and diseases of abnormal cellular proliferation and signal transduction.

BACKGROUND OF THE INVENTION

Guanine nucleotide binding proteins (GTP-binding proteins) participate in a wide range of regulatory functions in all organisms. They are present in all eukaryotic cells and function in processes including metabolism, cellular growth, differentiation, signal transduction, cytoskeletal organization, and intracellular vesicle transport and secretion. The GTP-binding proteins control a diverse sets of regulatory pathways and consequently, play a key role in the cell's ability to process and respond to information. Much of this information is provided to individual cells in the form of changes in concentration of hormones, growth factors, neuromodulators, or other molecules. When these molecules bind to transmembrane receptors, a signal is propagated to effector molecules by intracellular signal transducing proteins, many of which are members of the G-protein family.

The superfamily of GTP-binding proteins consists of several families including translational factors, heterotrimeric GTP-binding proteins involved in transmembrane signaling processes, protooncogenic ras proteins, and low-molecular weight (ras family) GTP-binding proteins.

Heterotrimeric GTP-binding proteins are composed of 3 subunits (α, β and γ) which, in the resting state, associate as a trimer at the inner face of the plasma membrane. The α subunits has a molecule of guanosine diphosphate (GDP) bound to it: stimulation of the G-protein by an activated receptor leads to its exchange for guanosine triphosphate (GTP). This results in the separation of the α from the β and γ subunits, which remain tightly associated as a dimer. Both the α and β-γ subunits are then able to interact with effectors, either individually or in a cooperative manner. The intrinsic GTPase activity of the α subunits hydrolyses the bound GTP to GDP. This returns the α subunit to its inactive conformation and allows it to reassociate with the β-γ subunits, which restores the system to its resting state (Kaziro, Y. (1991) Annu. Rev. Biochem. 60:349–400;).

Many distinct classes of α, β, and γ subunits have been identified in mammalian heterotrimeric GTP-binding proteins. The α-s class is sensitive to ADP-ribosylation by pertussis toxin which uncouples the receptor:G protein interaction. This uncoupling blocks signal transduction to receptors that decrease cAMP levels, which regulates ion channels and activates phospholipases. The inhibitory, α-I class, is also susceptible to modification by pertussis toxin which prevents α-I from lowering cAMP levels. Two novel classes refractory to pertussis toxin modification, are α-q which activates phospholipase C and α-12 which has sequence homology with the Drosophila gene *concertina* and may contribute to the regulation of embryonic development (Simon, M. I. (1991) Science 252:802–808). The β subunit sequences are highly conserved between species implying that they perform a fundamentally important role in the organization and function of G-protein linked systems (Van der Voorn L. (1992) Febs. Lett. 307 (2):131–134). The γ subunit primary structures are more variable than those of the γ subunits. They are often post-translationally modified by isoprenylation and carboxyl-methylation of a cysteine residue 4 amino acids from the C-terminus; this appears to be necessary for the interaction of the β-γ subunit with the membrane and with other GTP-binding proteins. The β-γ subunit has been shown to modulate the activity of isoforms of adenylyl cyclase, phospholipase C, and some ion channels. It is involved in receptor phosphorylation via specific kinases, and has been implicated in the p21ras-dependent activation of the MAP kinase cascade and the recognition of specific receptors by the GTP-binding proteins. (Clapham, D. E. (1993) Nature 365:403–406).

The low molecular weight GTP-binding proteins regulate cell growth, cell cycle control, protein secretion, and intracellular vesicle interaction. At least sixty members of this ras-related superfamily have been identified and are currently grouped into the four subfamilies of ras, rho, ran, and rab. They consist of single polypeptides of 21–30 kD which, like the α subunit of the heterotrimeric GTP-binding proteins, are able to bind and to hydrolyze GTP, thus cycling from an inactive to an active state. These GTP-binding proteins respond to extracellular signals from receptors and activating proteins by transducing mitogenic signals involved in various cell functions. (Tavitian, A. (1995) C. R. Seances Soc. Biol. Fil. 189:7–12).

Activated ras genes were initially found in human cancers and subsequent studies confirmed that ras function is critical in the determination of whether cells continue to grow or become terminally differentiated. Stimulation of cell surface receptors activates ras which, in turn, activates cytoplasmic kinases. The kinases translocate to the nucleus and activate key transcription factors that control gene expression and protein synthesis. (Barbacid, M. (1987)Ann. Rev Biochem. 56:779–827, Treisman, R. (1994) Curr. Opin. Genet. Dev. 4:96–98).

The other members of the small G-protein superfamily have roles in signal transduction that vary with the function of the activated genes and the locations of the GTP-binding proteins that initiate the activity. The rho GTP-binding proteins control signal transduction pathways that link growth factor receptors to actin polymerization which is necessary for normal cellular growth and division. The rab proteins control the translocation of vesicles to and from membranes for protein localization, protein processing, and secretion. The ran GTP-binding proteins are located in the nucleus of cells and have a key role in nuclear protein import, the control of DNA synthesis, and cell-cycle progression (Hall, A. (1990) Science 249:635–640, Scheffzek, K. et al. (1995) Nature 374:378–381).

The discovery of polynucleotides encoding new GTP-binding proteins, and the molecules themselves, provides the means to investigate abnormal cell proliferation and signal transduction processes. Discovery of novel molecules related to human GTP-binding proteins and the polynucleotides encoding them satisfies a need in the art by providing new diagnostic or therapeutic compositions useful in diagnosis, prevention, and treatment of disorders and diseases of abnormal cellular proliferation and signal transduction.

SUMMARY OF THE INVENTION

The present invention features three novel human GTP-binding proteins, designated individually as BND-1, BND-2 and BND-3 and collectively as BND, and characterized as having similarity to human G25K, human rab30, and mouse GTP-binding protein.

Accordingly, the invention features substantially purified BND-1, BND-2, and BND-3 having the anino acid sequences; SEQ ID NO:1, SEQ ID NO:3, and SEQ ID NO:5, respectively.

One aspect of the invention features isolated and substantially purified polynucleotides that encode BND-1, BND-2, and BND-3. In a particular aspect, the polynucleotides are the nucleotide sequences of SEQ ID NO:2, SEQ ID NO:4, or SEQ ID NO:6, respectively.

The invention also features a polynucleotide sequence comprising the complement of SEQ ID NO:2, SEQ ID NO:4, SEQ ID NO:6, or variants thereof. In addition, the invention features polynucleotide sequences which hybridize under stringent conditions to SEQ ID NO:2, SEQ ID NO:4, or SEQ ID NO:6.

The invention additionally features nucleic acid sequences encoding polypeptides, oligonucleotides, peptide nucleic acids (PNA), fragments, portions or antisense molecules thereof, and expression vectors and host cells comprising polynucleotides that encode BND. The present invention also features antibodies which bind specifically to BND, and pharmaceutical compositions comprising substantially purified BND. The invention also features the use of agonists and antagonists of BND.

BRIEF DESCRIPTION OF THE FIGURES

FIGS. 1A and 1B show the amino acid sequence (SEQ ID NO:1) and nucleic acid sequence (SEQ ID NO:2) of BND-1. The alignment was produced using MACDNASIS PRO™ software (Hitachi Software Engineering Co., Ltd., San Bruno, Calif.).

FIGS. 2A and 2B show the amino acid sequence (SEQ ID NO:3) and nucleic acid sequence (SEQ ID NO:4) of BND-2.

FIGS. 3A and 3B show the amino acid sequence (SEQ ID NO:5) and nucleic acid sequence (SEQ ID NO:6) of BND-3.

FIG. 4 shows the amino acid sequence alignment between BND-1 (SEQ ID NO:1) and human G25K (GI 183490). The alignment was produced using the multisequence alignment program of DNASTAR™ software (DNASTAR Inc, Madison, Wis.).

FIG. 5 shows the amino acid sequence alignment between BND-2 (SEQ ID NO:3) and human rab30 (GI 1457955).

FIG. 6 shows the amino acid sequence alignment between BND-3 (SEQ ID NO:5) and mouse GTP-binding protein (GI 240986).

DESCRIPTION OF THE INVENTION

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

Nucleic acid sequence, as used herein, refers to an oligonucleotide, nucleotide, or polynucleotide, and fragments or portions thereof, and to DNA or RNA of genomic or synthetic origin which may be single- or double-stranded and represent the sense or antisense strand. Similarly, "amino acid sequence", as used herein, refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "proteins" are not meant to limit the amino acid sequence to the complete, native amino acid sequence associated with the recited protein molecule. "Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

BND, as used herein, refers to the amino acid sequences of substantially purified BND obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEW™ Fragment Assembly system (GCG, Madison, Wis.), or which has been both extended and assembled.

A "variant" of BND, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic BND, or any oligopeptide thereof, to induce a specific immune response in appropriate animals or cells and to bind with specific antibodies.

The term "agonist", as used herein, refers to a molecule which, when bound to BND, causes a change in BND which modulates the activity of BND. Agonists may include proteins, nucleic acids, carbohydrates, or any other molecules which bind to BND.

The terms "antagonist" or "inhibitor", as used herein, refer to a molecule which, when bound to BND, blocks or modulates the biological or immunological activity of BND. Antagonists and inhibitors may include proteins, nucleic acids, carbohydrates, or any other molecules which bind to BND.

The term "modulate", as used herein, refers to a change or an alteration in the biological activity of BND. Modulation may be an increase or a decrease in protein activity, a change in binding characteristics, or any other change in the biological, functional or immunological properties of BND.

The term "mimetic", as used herein, refers to a molecule, the structure of which is developed from knowledge of the structure of BND or portions thereof and, as such, is able to effect somc or all of the actions of G-protein-like molecules.

The term "derivative", as used herein, refers to the chemical modification of a nucleic acid encoding BND or the encoded BND. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primers, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "similarity", as used herein, refers to a degree of complementarity. There may be partial homology or complete similarity (i.e., identity). A partially complementary sequence is one that at least partially inhibits an identical sequence from hybridizing to a target nucleic acid; it is referred to using the functional term "substantially similar." The inhibition of hybridization of the completely complementary sequence to the target sequence may be examined using a hybridization assay (Southern or northern blot, solution hybridization and the like) under conditions of low stringency. A substantially similar sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second noncomplementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human BND-1 and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to protein in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding BND or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2, SEQ ID NO:4, or SEQ ID NO:6 by northern analysis is indicative of the presence of mRNA encoding BND in a sample and thereby correlates with expression of the transcript from the polynucleotides encoding the protein.

"Alterations" in the polynucleotide of SEQ ID NO:2, SEQ ID NO:4, or SEQ ID NO:6, as used herein, comprise any alteration in the sequence of polynucleotides encoding BND including deletions, insertions, and point mutations that may be detected using hybridization assays. Included within this definition is the detection of alterations to the genomic DNA sequence which encodes BND (e.g., by alterations in the pattern of restriction fragment length polymorphisms capable of hybridizing to SEQ ID NO:2, SEQ ID NO:4, or SEQ ID NO:6), the inability of a selected fragment of SEQ ID NO:2, SEQ ID NO:4, or SEQ ID NO:6 to hybridize to a sample of genomic DNA (e.g., using allele-specific oligonucleotide probes), and improper or unexpected hybridization, such as hybridization to a locus other than the normal chromosomal locus for the polynucleotide sequence encoding BND (e.g., using fluorescent in situ hybridization (FISH) to metaphase chromosomes spreads).

As used herein, the term "antibody" refers to intact molecules as well as fragments thereof, such as Fa, $F(ab)_2$, and Fv, which are capable of binding the epitopic determinant. Antibodies that bind BND polypeptides can be prepared using intact polypeptides or fragments containing small peptides of interest as the immunizing antigen. The polypeptide or peptide used to immunize an animal can be derived from the translation of mRNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of novel human GTP-binding proteins (BND-1, BND-2, and BND-3, collectively referred to as BND), the polynucleotides encoding BND, and the use of these compositions for the diagnosis, prevention and treatment of disorders and diseases of abnormal cellular proliferation and signal transduction.

Nucleic acid sequence encoding the human BND-1 of the present invention was first identified in Incyte Clone 113700 from a testicular tissue cDNA library (TESTNOT01) through a computer-generated search for amino acid sequence alignments. A consensus sequence, SEQ ID NO:2, was derived from the following overlapping and/or extended nucleic acid sequences (cDNA library from which derived): Incyte Clones 113700 (TESTNOT01) and 179322 (PLACNOB01).

Nucleic acid sequence encoding the human BND-2 of the present invention was first identified in Incyte Clone 583177 from a prostate tissue cDNA library (PROSNOT02) through a computer-generated search for amino acid sequence alignments. A consensus sequence, SEQ ID NO:4, was derived from the following overlapping and/or extended nucleic acid sequences (and cDNA library from which derived): Incyte Clones 583177 and 582201 (PROSNOT02); 899921 and 902624 (BRSTTUT03); 992064 (COLNNOT 11); 078316 (SYNORAB01); and 1424482 (BEPINON01).

Nucleic acid sequence encoding the human BND-3 of the present invention was first identified in Incyte Clone 627051, from a paraganglionic tumor tissue cDNA library (PGANNOT01) through a computer-generated search for amino acid sequence alignments. A consensus sequence, SEQ ID NO:6, was derived from the following overlapping and/or extended nucleic acid sequences (cDNA library from which derived): Incyte Clones 627051 (PGANNOT01); 586525 (UTRSNOT01); 719363 (SYNOOAT01); 836241 and 837631 (PROSNOT07); 1228396 (COLNOT01); 1316240 (BLADTUT02); 1378809 (LUNGNOT01); 855922 and 856810 (NGANNOT01); 929744 (CERVNOT01); 628180 and 955099 (KIDNNOT05); 994996 and 1001874 (BRSTNOT03); and 147085 (FIBRNOT02).

In one embodiment, the invention encompasses the novel human GTP-binding protein BND-1, a polypeptide comprising the amino acid sequence of SEQ ID NO:1, and shown in FIGS. 1A, 1B. BND-1 is 182 amino acids in length and, as shown in FIG. 4, BND-1 has chemical and structural homology with human G25K (GI 183490). In particular, BND-1 shares 53% identity with G 183490. BND-1 contains two GTP binding domains spanning amino acids $L_{38}$ to $Q_{46}$ and $L_{97}$ to $L_{104}$. The amino acid motif which defines these domains, consisting of a P-loop structure, is conserved between BIND-1 and GI 183490.

In another embodiment, the invention encompasses the novel human GTP-binding protein BND-2, a polypeptide comprising the amino acid sequence of SEQ ID NO:3, as shown in FIGS. 2A, 2B. BND-2 is 186 amino acids in length and, as shown in FIG. 5, BND-2 has chemical and structural homology with human rab30 (GI 1020151). In particular, BND-2 shares 32% homology with GI 1020151. BND-2 contains three GTP binding domains spanning amino acids $V_{16}$ to $T_{19}$, $V_{119}$, to $D_{126}$, and $E_{151}$ to $K_{155}$, which are also seen in GI 1020151.

In an additional embodiment, the invention encompasses the novel human GTP-binding proteins BND-3, a polypeptide comprising the amino acid sequence of SEQ ID NO:5, as shown in FIGS. 3A, 3B. BND-3 is 169 amino acids in length and, as shown in FIG. 6, BND-3 has chemical and structural homology with mouse GTP-binding protein (GI 240986). In particular, BND-3 and GI 240986 share 74% identity. BND-3 contains two GTP binding domains defined by amino acids $L_{13}$ to $F_{24}$ and $F_{72}$ to $L_{80}$ which are also seen in GI 240986.

The invention also encompasses BND variants. A preferred BND variant is one having at least 80%, and more preferably 90%, amino acid sequence similarity to the BND amino acid sequence (SEQ ID NO:1, SEQ ID NO:3, or SEQ ID NO:5). A most preferred BND variant is one having at least 95% amino acid sequence similarity to SEQ ID NO:1, SEQ ID NO:3, or SEQ ID NO:5.

The invention also encompasses polynucleotides which encode BND. Accordingly, any nucleic acid sequence which encodes the amino acid sequence of BND can be used to generate recombinant molecules which express BND. In a particular embodiment, the invention encompasses the polynucleotide comprising the nucleic acid of SEQ ID NO:2, SEQ ID NO:4, or SEQ ID NO:6 as shown in FIGS. 1A and 1B, 2A and 2B, and 3A and 3B.

It will be appreciated by those skilled in the art that as a result of the degeneracy of the genetic code, a multitude of nucleotide sequences encoding BND, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring BND, and all such variations are to be considered as being specifically disclosed.

Although nucleotide sequences which encode BND and its variants are preferably capable of hybridizing to the nucleotide sequence of the naturally occurring BND under appropriately selected conditions of stringency, it may be advantageous to produce nucleotide sequences encoding BND or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding BND and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode BND and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding BND or any portion thereof.

Also encompassed by the invention are polynucleotide sequences that are capable of hybridizing to the claimed nucleotide sequences, and in particular, those shown in SEQ ID NO:2, SEQ ID NO:4, or SEQ ID NO:6, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–11), and may be used at a defined stringency.

Altered nucleic acid sequences encoding BND which are encompassed by the invention include deletions, insertions, or substitutions of different nucleotides resulting in a polynucleotide that encodes the same or a functionally equivalent BND. The encoded protein may also contain deletions, insertions, or substitutions of amino acid residues which produce a silent change and result in a functionally equivalent BND. Deliberate amino acid substitutions may be made on the basis of similarity in polarity, charge, solubility, hydrophobicity, hydrophilicity, and/or the amphipathic nature of the residues as long as the biological activity of BND is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the gene encoding BND. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Kienow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding BND may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO® 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER™ libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER™ and SEQUENCE NAVIGATOR™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode BND, or fusion proteins or functional equivalents thereof, may be used in recombinant DNA molecules to direct expression of BND in appropriate host cells. Due to the inherent degeneracy of the genetic code, other DNA sequences which encode substantially the same or a functionally equivalent amino acid sequence may be produced and these sequences may be used to clone and express BND.

As will be understood by those of skill in the art, it may be advantageous to produce BND-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter sequences encoding BND for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, to alter glycosylation patterns, to change codon preference, to produce splice variants, or to introduce mutations, and so forth.

In another embodiment of the invention, natural, modified, or recombinant polynucleotides encoding BND may be ligated to a heterologous sequence to encode a fusion protein. For example, to screen peptide libraries for inhibitors of BND activity, it may be useful to encode a chimeric BND protein that can be recognized by a commercially available antibody. A fusion protein may also be engineered to contain a cleavage site located between a sequence encoding BND and the heterologous protein sequence, so that BND may be cleaved and purified away from the heterologous moiety.

In another embodiment, sequences encoding BND may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of BND, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of BND, or any part thereof, may be altered during direct synthesis and/or combined using chemical methods with sequences from other proteins, or any part thereof, to produce a variant polypeptide.

In order to express a biologically active BND, the nucleotide sequences encoding BND or functional equivalents, may be inserted into appropriate expression vectors, i.e., a vector which contains the necessary elements for the transcription and translation of the inserted coding sequence.

Methods which are well known to those skilled in the art may be used to construct expression vectors containing sequences encoding BND and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding BND. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT® phagemid (Stratagene, LaJolla, Calif.) or PSPORTI™ plasmid (Gibco BRL), and the like, may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding BND, vectors based on SV40 or EBV may be used with an appropriate selectable marker.

In bacterial systems, a number of expression vectors may be selected depending upon the use intended for BND. For example, when large quantities of BND are needed for the induction of antibodies, vectors which direct high level expression of fusion proteins that are readily purified may be used. Such vectors include, but are not limited to, the multifunctional *E. coli* cloning and expression vectors such as BLUESCRIPT® (Stratagene), in which the sequence encoding BND may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of a sequence encoding BND may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunits of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express BND. For example, in one such system, *Autographa californica* nuclear polyhedrosis virus (AcNPV) is used as a vector to express foreign genes in *Spodoptera frugiperda* cells or in Trichoplusia larvae. The sequences encoding BND may be cloned into a non-essential region of the virus, such as the polyhedrin gene, and placed under control of the polyhedrin promoter. Successful insertion of BND will render the polyhedrin gene inactive and produce recombinant virus lacking coat protein. The recombinant viruses may then be used to infect, for example, *S. frugiperda* cells or Trichoplusia larvae in which BND may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding BND may be ligated into an adenovirus transcription/translation complex consisting of the late promoter and tripartite leader sequence. Insertion in a non-essential E1 or E3 region of the viral genome may be used to obtain a viable virus which is capable of expressing BND in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding BND. Such signals include the ATG initiation codon and adjacent sequences. In cases where sequences encoding BND, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express BND may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$ or $aprt^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding BND is inserted within a marker gene sequence, recombinant cells containing sequences encoding BND can be identified by the absence of marker gene function. Alternatively, a marker gene can be placed in tandem with a sequence encoding BND under the control of a single promoter. Expression of the marker gene in response to induction or selection usually indicates expression of the tandem gene as well.

Alternatively, host cells which contain sequences encoding and expressing BND may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of the nucleic acid or protein.

The presence of polynucleotide sequences encoding BND can be detected by DNA—DNA or DNA-RNA hybridization or amplification using probes or portions or fragments of polynucleotides encoding BND. Nucleic acid amplification based assays involve the use of oligonucleotides or oligomers based on the sequences encoding BND to detect transformants containing DNA or RNA encoding BND. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of BND, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on BND is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding BND include oligolabeling, nick translation, end-labeling or PCR amplification using a labeled nucleotide. Alternatively, sequences encoding BND, or any portion thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits from Pharmacia & Upjohn (Kalamazoo, Mich.); Promega (Madison, Wis.); and U.S. Biochemical Corp. (Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding BND may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode BND may be designed to contain signal sequences which direct secretion of BND through a prokaryotic or eukaryotic cell membrane. Other recombinant constructions may be used to join sequences encoding BND to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and BND may be used to facilitate purification. One such expression vector provides for expression of a fusion protein containing BND and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3: 263–281) while the enterokinase cleavage site provides a means for purifying BND from the fusion protein. A discussion of vectors which contain fusion proteins is provided in Kroll, D. J. et al. (1993; DNA Cell Biol. 12:441–453).

In addition to recombinant production, fragments of BND may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of BND may be chemically synthesized separately and combined using chemical methods to produce the full length molecule.

THERAPEUTICS

Based on the chemical and structural homology between BND-1 (SEQ ID NO:1) and human G25K (GI 183490), BND-2 (SEQ ID NO:3) and rab30 (GI 1457955), and BND-3 and mouse GTP-binding protein (GI 240986), BND appears to play a role in cell proliferation and signal transduction, and thus, may be used therapeutically for diseases and disorders involving these processes.

BND-1 appears to be involved in the regulation of the cell cycle, cell growth, cell signaling, and cellular cytoskeletal organization which are key factors in neoplastic disease, arthritic disease, autoimmune disease, inflammatory disease, and diseases of abnormal tissue proliferation. Expression of BND-1 is associated with aberrant tissue proliferation, autoimmune and inflammatory conditions. Therefore, in one embodiment, vectors capable of expressing antisense to the nucleic acid sequence encoding BND-1 or a fragment or derivative thereof may be administered to a subject to prevent or treat neoplastic disease, arthritic disease, autoimmune disease, inflammatory disease, and diseases of abnormal tissues proliferation including, but not limited to, cancer, leukemia, lymphoma, endometriosis, atherosclerosis, lupus erythematosus, and arthritis.

In another embodiment, antagonists or inhibitors of BND-1 may be administered to a subject to treat any of the conditions described above. In one aspect, antibodies which are specific for BND-1 may be used directly as an antagonist, or indirectly as a targeting or delivery mechanism for administering a pharmaceutical agent to cells or tissue which express BND-1.

Based on the chemical and structural homology between BND-2 (SEQ ID NO:3) and rab30 (GI 1457955), and BND-3 and mouse GTP-binding protein (GI 240986), BND-2 and BND-3 appear to be involved in the regulation of the cellular vesicle targeting; membrane transfer and fusion; or protein processing, targeting and secretion. Disorders and diseases involving these functions may include, but are not limited to, diminished neurotransmitter and hormone secretion, lysosomal storage diseases, immunological disorders, and cancer.

In one embodiment, vectors expressing antisense to the nucleic acid sequence encoding BND-2 or a fragment or derivative thereof may be administered to a subject to treat diseases or conditions associated with abnormal membrane transfer and fusion or abnormal protein processing, targeting, and secretion.

In another embodiment, antagonists or inhibitors of BND-2 may be administered to a subject to treat diminished neurotransmitter and hormone secretion, lysosomal storage diseases, immunological disorders, and cancer. In one aspect, antibodies which are specific for BND-2 may be used directly as an antagonist, or indirectly as a targeting or delivery mechanism for administering a pharmaceutical agent to cells or tissue which express BND-2.

In another embodiment, vectors expressing BND-2 may be administered to a subject to treat disorders resulting from a deficiency of BND-2 expression which may include, but are not limited to, diminished neurotransmitter and hormone secretion, lysosomal storage diseases, immunological disorders, and cancer.

In one embodiment, vectors expressing antisense to the nucleic acid sequence encoding BND-3 or a fragment or derivative thereof may be administered to a subject to treat diseases or conditions associated with abnormal membrane transfer and fusion, abnormal protein processing, protein targeting and secretion.

In another embodiment, antagonists or inhibitors of BND-3 may be administered to a subject to treat diminished neurotransmitter and hormone secretion, lysosomal storage diseases, immunological disorders, and cancer. In one aspect, antibodies which are specific for BND-3 may be used directly as an antagonist, or indirectly as a targeting or delivery mechanism for administering a pharmaceutical agent to cells or tissue which express BND-3.

In another embodiment, vectors expressing BND-3 may be administered to a subject to treat disorders resulting from a deficiency of BND-3 expression which may include, but are not limited to, diminished neurotransmitter and hormone secretion, lysosomal storage diseases, immunological disorders, and cancer.

In other embodiments, any of the therapeutic proteins, antagonists, antibodies, agonists, antisense sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Agonists or inhibitors of BND-1, BND-2, or BND-3 may be produced using methods which are generally known in the art. In particular, purified BND may be used to produce antibodies or to screen libraries of pharmaceutical agents to identify those which specifically bind BND.

Antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with BND or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and rdinitrophenol. Among adjuvants used in humans, BCG (bacilli Calmette-Guerin) and *Corynebacterium parvum* are especially preferable.

It is preferred that the peptides, fragments, or oligopeptides used to induce antibodies to BND have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of BND amino acids may be fused with those of another protein such as keyhole limpet hemocyanin and antibody produced against the chimeric molecule.

Monoclonal antibodies to BND may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J Immunol. Methods 81:31–42; Cote, R. J. et al. (1983) Proc. Natl. Acad. Sci. 80:2026–2030; Cole, S. P. et al. (1985) Mol Cell Biol. 62:109–120.

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–55; Neuberger, M. S. et al. (1984) Nature 312:604–8; Takeda, S. et al. (1985) Nature 314:452–4). Alternatively, techniques described for the production of single chain antibodies may be adapted, using methods known in the art, to produce BND-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833–37; Winter, G. et al. (1991) Nature 349:293–9).

Antibody fragments which contain specific binding sites for BND may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–81).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between BND and its specific antibody. A two-site, monoclonal-based immunoassay utilizing monoclonal antibodies reactive to two non-interfering BND epitopes is preferred, but a competitive binding assay may also be employed (Maddox, supra).

In another embodiment of the invention, the polynucleotides encoding BND, or any fragment thereof, or antisense molecules, may be used for therapeutic purposes. In one aspect, antisense to the polynucleotide encoding BND may be used in situations in which it would be desirable to block the transcription of mRNA. In particular, cells may be transformed with sequences complementary to polynucleotides encoding BND. Thus, antisense sequences may be used to modulate BND activity, or to achieve regulation of gene function. Such technology is now well known in the art, and sense or antisense oligomers or larger fragments, can be designed from various locations along the coding or control regions of sequences encoding BND.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense polynucleotides of the gene encoding BND. These techniques are described both in Sambrook et al. (supra) and in Ausubel et al. (supra).

Genes encoding native BND can be turned off by transforming a cell or tissue with expression vectors which express high levels of the polynucleotide, or fragment thereof, which encodes BND. Such constructs may be used to introduce untranslatable sense or antisense sequences into a cell. Even in the absence of integration into the genomic DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding BND, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic*

*Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding BND.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding BND. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of BND, antibodies to BND, mimetics, agonists, antagonists, or inhibitors of BND. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of BND, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example BND or fragments thereof, antibodies of BND, agonists, antagonists or inhibitors of BND, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be pecific to particular cells, conditions, locations, etc.

DIAGNOSTICS

In another embodiment, antibodies which specifically bind BND may be used for the diagnosis of conditions or diseases characterized by expression of BND, or in assays to monitor patients being treated with BND, agonists, antagonists or inhibitors. The antibodies useful for diagnostic purposes may be prepared in the same manner as those described above for therapeutics. Diagnostic assays for BND include methods which utilize the antibody and a label to detect BND in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring BND are known in the art and provide a basis for diagnosing altered or abnormal levels of BND expression. Normal or standard values for BND expression are established by combining body fluids or cell extracts taken from normal manmmalian subjects, preferably human, with antibody to BND under conditions suitable for complex formation. The amount of standard complex formation may be quantified by various methods, but preferably by photometric means. Quantities of BND expressed in subject samples, control and disease, from biopsied tissues are compared with the standard values. Deviation between standard and subject values establishes the parameters for diagnosing disease.

In another embodiment of the invention, the polynucleotides encoding BND may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of BND may be correlated with disease. The diagnostic assay may be used to distinguish between absence, presence, and excess expression of BND, and to monitor regulation of BND levels during therapeutic intervention.

In one aspect, hybridization with PCR probes which are capable of detecting polynucleotide sequences, including genomic sequences, encoding BND or closely related molecules, may be used to identify nucleic acid sequences which encode BND. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding BND, alleles, or related sequences.

Probes may also be used for the detection of related sequences, and should preferably contain at least 50% of the nucleotides from any of the sequences encoding BND. The hybridization probes of the subject invention may be DNA or RNA and derived from the nucleotide sequences of SEQ ID NO:2, SEQ ID NO:4, or SEQ ID NO:6 or from genomic sequence including promoter, enhancer elements, and introns of the naturally occurring BND.

Means for producing specific hybridization probes for DNAs encoding BND include the cloning of nucleic acid sequences encoding BND or BND derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding BND may be used for the diagnosis of conditions or diseases which are associated with expression of BND. Examples of such conditions or diseases include, but are not limited to, tumors, leukemia, lymphoma, hemolytic anemia, lupus erythematosus, rheumatoid arthritis, endometriosis, diminished neurotransmitter and hormone secretion, lysosomal storage diseases, immunological disorders, and cancer. The polynucleotide sequences encoding BND may be used in Southern or northern analysis, dot blot, or other membrane-based technologies; in PCR technologies; or in dip stick, pin, ELISA or chip assays utilizing fluids or tissues from patient biopsies to detect altered BND expression. Such qualitative or quantitative methods are well known in the art.

In a particular aspect, the nucleotide sequences encoding BND may be useful in assays that detect activation or induction of various cancers, particularly those mentioned above. The nucleotide sequences encoding BND may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding BND in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of BND, a normal or standard profile for expression is established. This may be accomplished by combining body fluids or cell extracts taken from normal subjects, either animal or human, with a sequence, or a fragment thereof, which encodes BND, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively low amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding BND may involve the use of PCR. Such oligomers may be chemically synthesized, generated enzymatically, or produced from a recombinant source. Oligomers will preferably consist of two nucleotide sequences, one with sense orientation (5'–>3') and another with antisense (3'<–5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of BND include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or calorimetric response gives rapid quantitation.

In another embodiment of the invention, the nucleic acid sequence which encodes BND may also be used to generate hybridization probes which are useful for mapping the naturally occurring genomic sequence. The sequence may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome CDNA libraries as reviewed in Price, C. M. (1993) Blood Rev. 7:127–134, and Trask, B. J. (1991) Trends Genet. 7:149–154.

FISH (as described in Verma, R. S. et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding BND on a physical chromosomal map and a specific disease , or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, BND, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between BND and the agent being tested, may be measured.

Another technique for drug screening which may be used provides for high throughput screening of compounds having suitable binding affinity to the protein of interest as described in published PCT application WO84/03564. In this method, as applied to BND large numbers of different small test compounds are synthesized on a solid substrate, such as plastic pins or some other surface. The test compounds are reacted with BND, or fragments thereof, and washed. Bound BND is then detected by methods well known in the art. Purified BND can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding BND specifically compete with a test compound for binding BND. In this manner, the antibodies can be used to detect the presence of any peptide which shares one or more antigenic determinants with BND.

In additional embodiments, the nucleotide sequences which encode BND may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I DNA Library Construction

TESTNOT01

Tissue was obtained from a 37-year-old Caucasian male (lot no. 94-267); Keystone Skin Bank, International Institute for the Advancement of Medicine (Exton, Pa.). The tissue was flash frozen, ground using a mortar and pestle and was lysed immediately in buffer containing guanidinium isothiocyanate. Lysis was followed by several phenol chloroform extractions and ethanol precipitation. Polyadenylated RNA was isolated using biotinylated oligo d(T) primer and streptavidin coupled to a paramagnetic particle (Promega Corp., Madison, Wis.) and sent to Stratagene.

Stratagene prepared the cDNA library using oligo d(T) priming. Synthetic adapter oligonucleotides were ligated onto the cDNA molecules enabling them be inserted into the UNI-ZAP™ vector system (Stratagene).

The quality of the cDNA library was screened using DNA probes, and the PBLUESCRIPT® phagemid (Stratagene) was excised. Subsequently, the custom-constructed library phage particles were infected into *E. coli* host strain XLI-BLUE® (Stratagene). Alternative unidirectional vectors might include, but are not limited to, pcDNAI (Invitrogen, San Diego, Calif.) and pSHlox-1 (Novagen, Madison, Wis.).

PROSNOT01

The prostate tissue used for library construction was obtained from a 50 year-old male. The tissue was flash frozen, ground using a mortar and pestle, extracted four times with acid phenol pH 4.0, and centrifuged over a CsCl cushion using an Beckman SW28 rotor in a Beckman L8-70M Ultracentrifuge (Beckman Instruments). The RNA was precipitated using 0.3M sodium acetate and 2.5 volumes of ethanol, resuspended in water, and DNase treated for 15 min at 37° C. The RNA was isolated using the Qiagen Oligotex kit (QIAGEN Inc, Chatsworth Calif.) and used to construct the CDNA library.

PGANNOT01

The tissue used for paraganglion cDNA library construction was obtained from a 46 year-old male. The frozen tissue was homogenized and lysed in guanidinium isothiocyanate solution using a Brinkmann Homogenizer Polytron PT-3000 (Brinkmann Instruments, Westbury N.J.). The lysate was centrifuged over a 5.7M CsCl cushion using an Beckman SW28 rotor in a Beckman L8-70M Ultracentrifuge (Beckman Instruments) for 18 hours at 25,000 rpm at ambient temperature. The RNA was extracted twice with acid phenol pH 4.0 following Stratagene's RNA isolation protocol, precipitated using 0.3M sodium acetate and 2.5 volumes of ethanol, resuspended in DEPC-treated water, and DNase treated for 15 min at 37° C. The reaction was stopped with an equal volume of acid phenol and the RNA was isolated using the Qiagen Oligotex kit and used to construct the cDNA library.

The RNA was handled according to the recommended protocols in the SuperScript Plasmid System for cDNA Synthesis and Plasmid Cloning (catalog #18248-013; Gibco/BRL), and cDNAs were ligated into PSPORTI. The plasmid PSPORTI was subsequently transformed into DH5A™ competent cells (Cat. #18258-012, Gibco/BRL).

II Isolation of cDNA Clones

TESTNOT01

The phagemid forms of the individual cDNA clones were obtained by the in vivo excision process, in which the host bacterial strain was co-infected with both the library phage and an f1 helper phage. Polypeptides or enzymes derived from both the library-containing phage and the helper phage nicked the DNA, initiated new DNA synthesis from defined sequences on the target DNA, and created a smaller, single stranded circular phagemid DNA molecule that included all DNA sequences of the pBluescript phagemid and the cDNA insert. The phagemid DNA was released from the cells and purified, and used to reinfect fresh host cells (SOLR, Stratagene) where double stranded DNA was produced. Because the phagemid carries the gene for β-lactamase, the newly transformed bacteria were selected on medium containing ampicillin.

Phagemid DNA was purified using the QIAWELL™ -8 Plasmid Purification system (QIAGEN). The DNA was eluted from the purification resin and prepared for DNA sequencing and other analytical manipulations.

PROSNOT01 and PGANNOT01

Plasmid DNA was released from the cells and purified using the Miniprep Kit (Catalogue #77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Catalog #22711, LIFE TECHNOLOGIES™, Gaithersburg Md.) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs for all three libraries were sequenced by the method of Sanger F and A. R. Coulson (1975; J Mol Biol 94:441f), using a Hamilton Micro Lab 2200 (Hamilton, Reno, Nev.) in combination with four Peltier Thermal Cyclers (PTC200 from MJ Research, Watertown Mass.) and Applied Biosystems 377 or 373 DNA Sequencing Systems (Perkin Elmer), and reading frame was determined.

III Homology Searching of cDNA Clones and Their Deduced Proteins

Each cDNA was compared to sequences in GenBank using a search algorithm developed by Applied Biosystems and incorporated into the INHERIT™ 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul, S. F. et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\%\ \text{sequence identity} \times \%\ \text{maximum BLAST score}/100$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding BND occurs. Abundance and percent abundance are also reported. Abundance directly reflects the number of times a particular transcript is represented in a cDNA library, and percent abundance is abundance divided by the total number of sequences examined in the cDNA library.

V Extension of Polynucleotides Encoding BND to Full Length or to Recover Regulatory Sequences Polynucleotides encoding BND (SEQ ID NO:2, SEQ ID NO:4, or SEQ ID NO:6) are used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M.J. Research, Watertown, Mass.) and the following parameters:

Step 1 94° C. for 1 min (initial denaturation)

Step 2 65° C. for 1 min

Step 3 68° C. for6 min

Step 4 94° C. for 15 sec

Step 5 65° C. for 1 min

Step 6 68° C. for 7 min

Step 7 Repeat step 4–6 for 15 additional cycles

Step 8 94° C. for 15 sec

Step 9 65° C. for 1 min

Step 10 68° C. for 7:15 min

Step 11 Repeat step 8–10 for 12 cycles

Step 12 72° C. for 8 min

Step 13 4° C. (and holding)

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQuick Kit (Qiagen Inc.). After recovery of the DNA, Kienow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent *E. coli* cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2× Carb. The following day, several colonies are randomly picked from each plate and cultured in 150 μl of liquid LB/2× Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

Step 1 94° C. for 60 sec

Step 2 94° C. for 20 sec

Step 3 55° C. for 30 sec

Step 4 72° C. for 90 sec

Step 5 Repeat steps 2–4 for an additional 29 cycles

Step 6 72° C. for 180 sec

Step 7 4° C. (and holding)

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2, SEQ ID NO:4, or SEQ ID NO:6 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 μCi of [$\gamma$-$^{32}$-P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

Antisense molecules to the sequence encoding BND, or any part thereof, is used to inhibit in vivo or in vitro expression of naturally occurring BND. Although use of antisense oligonucleotides, comprising about 20 base-pairs, is specifically described, essentially the same procedure is used with larger cDNA fragments. An oligonucleotide based on the sequences encoding BND is used to inhibit expression of naturally occurring BND. The complementary oligonucleotide is designed from the most unique 5' sequence as shown in and used either to inhibit transcription by preventing promoter binding to the upstream nontranslated sequence or translation of a transcript encoding BND by preventing the ribosome from binding. Using an appropriate portion of the signal and 5' sequence of SEQ ID NO:2, SEQ ID NO:4, or SEQ ID NO:6, an effective antisense oligonucleotide includes any 15–20 nucleotides spanning the region which translates into the signal or 5' coding sequence of the polypeptide as shown in FIGS. 1A and 1B, 2A and 2B, and 3A and 3B.

VIII Expression of BND

Expression of BND is accomplished by subcloning the cDNAs into appropriate vectors and transforming the vectors into host cells. In this case, the cloning vector, PSPORTI previously used for the generation of the cDNA library is used to express BND in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of BND into the bacterial growth media which can be used directly in the following assay for activity.

IX Demonstration of BND Activity

GTP-binding activity is assayed by incubating varying amounts of BND protein for 10 minutes at 30° C. in 50 mM Tris buffer, pH 7.5, containing 1 mM dithiothreitol, 1 mM EDTA, 1 $\mu$M (a-$^{32}$P), in the absence or presence of 100 $\mu$M of the following compounds: GTP, GDP, GTPγS, ATP, CTP, UTP, and TTP. Samples are passed through nitrocellulose filters and washed twice with a buffer consisting of 50 mM Tris-HCL, pH 7.8, 1 mM $NaN_3$, 10 mM $MgCl_2$, 1 mM EDTA, 0.5 mM dithiothreitol, 0.01 mM PMSF, and 200 mM NaCl. The filter-bound counts are determined by liquid scintillation. To determine GTPase activity, BND protein is incubated for 10 minutes at 37° C. in 50 mM Tris-HCL buffer, pH 7.8, containing 1 mM dithiothreitol, 2 mM EDTA, 10 $\mu$M (a-$^{32}$P), and 1 $\mu$M H-rab protein. GTPase activity is initiated by adding $MgCl_2$ to a final concentration of 10 mM. Samples are removed at various time points, mixed with an equal volume of ice-cold 0.5 mM EDTA, and frozen. Aliquots are spotted onto polyethyleneimine-cellulose thin layer chromatography plates, which are developed in 1M LiCl, dried, and autoradiographed.

X Production of BND Specific Antibodies

BND that is substantially purified using PAGE electrophoresis (Sambrook, supra), or other purification techniques, is used to immunize rabbits and to produce antibodies using standard protocols. The amino acid sequence deduced from SEQ ID NO:2, SEQ ID NO:4, or SEQ ID NO:6 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring BND Using Specific Antibodies

Naturally occurring or recombinant BND is substantially purified by immunoaffinity chromatography using antibodies specific for BND. An immunoaffinity column is constructed by covalently coupling BND antibody to an activated chromatographic resin, such as CnBr-activated Sepharose (Pharmacia & Upjohn). After the coupling, the resin is blocked and washed according to the manufacturer's instructions.

Media containing BND is passed over the immunoaffinity column, and the column is washed under conditions that allow the preferential absorbance of BND (e.g., high ionic strength buffers in the presence of detergent). The column is eluted under conditions that disrupt antibody/BND binding (eg, a buffer of pH 2–3 or a high concentration of a chaotrope, such as urea or thiocyanate ion), and BND is collected.

XII Identification of Molecules Which Interact with BND

BND or biologically active fragments thereof are labeled with $^{125}$I Bolton-Hunter reagent (Bolton, A. E. and W. M. Hunter (1973) Biochem. J. 133: 529–39). Candidate molecules previously arrayed in the wells of a multi-well plate are incubated with the labeled BND, washed and any wells with labeled BND complex are assayed. Data obtained using different concentrations of BND are used to calculate values for the number, affinity, and association of BND with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding a polypeptide comprising the amino acid sequence of SEQ ID NO:1.

2. A hybridization probe comprising the polynucleotide sequence of claim 1.

3. An isolated and purified polynucleotide sequence comprising SEQ ID NO:2.

4. A polynucleotide sequence which is fully complementary to SEQ ID NO:2.

5. A hybridization probe comprising the polynucleotide sequence of claim 4.

6. An expression vector containing the polynucleotide sequence of claim 1.

7. A host cell containing the vector of claim 6.

* * * * *